(12) United States Patent
Lombardin et al.

(10) Patent No.: US 6,709,675 B1
(45) Date of Patent: Mar. 23, 2004

(54) THIXOTROPIC FORMULATIONS FOR FILLING CAPSULES

(75) Inventors: Pascal Lombardin, Saint-Maurice (FR); Jean-Louis Grossiord, Saint-Germain-les-Corbeil (FR); Monique Seiller, Sceaux (FR); Elie Leverd, Castres (FR); Eric Goutay, Lauzerville (FR); Joël Bougaret, Lanta (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 09/743,248

(22) PCT Filed: Jul. 5, 1999

(86) PCT No.: PCT/FR99/01614
§ 371 (c)(1),
(2), (4) Date: Mar. 5, 2001

(87) PCT Pub. No.: WO00/01371
PCT Pub. Date: Jan. 13, 2000

(30) Foreign Application Priority Data

Jul. 7, 1998 (FR) .............................. 98 08664

(51) Int. Cl.$^7$ .......................... A61K 9/48; A61K 9/64; A61K 9/66; B01J 13/00
(52) U.S. Cl. ....................... 424/452; 424/455; 424/456; 424/453; 514/937; 516/99
(58) Field of Search ............................ 516/99; 424/452, 424/453, 455, 456; 514/937

(56) References Cited

U.S. PATENT DOCUMENTS

| 4,202,888 | A | | 5/1980 | Eckert et al. |
| H672 | H | * | 9/1989 | Baxter et al. ............ 424/453 X |
| 5,545,628 | A | * | 8/1996 | Deboeck et al. ......... 424/456 X |
| 5,993,858 | A | * | 11/1999 | Crison et al. ............ 424/455 X |
| 6,153,218 | A | * | 11/2000 | Barnwell et al. ........ 424/456 X |
| 6,171,615 | B1 | * | 1/2001 | Roussin et al. ......... 424/452 X |
| 6,346,537 | B1 | * | 2/2002 | Hata et al. .............. 424/452 X |
| 6,365,181 | B1 | * | 4/2002 | Matthews ............... 424/452 X |

FOREIGN PATENT DOCUMENTS

| EP | 0461290 B1 | 12/1991 |
| EP | 0517412 A1 | 12/1992 |
| FR | 2 365 338 | * 4/1978 |
| FR | 2761265 | 10/1998 |
| WO | WO9641622 | 12/1996 |

* cited by examiner

*Primary Examiner*—Richard D. Lovering
(74) *Attorney, Agent, or Firm*—The Firm of Hueschen and Sage

(57) ABSTRACT

The invention concerns liquid or pasty thixotropic compositions containing an active substance for filling capsules at room temperature. The compositions become fluid by the effect of shearing when they pass through the filling nozzle, then recover their consistency with sufficient intensity and rapidity to prevent, after filling any leak between the two capsule parts. Said compositions are characterized in that their rheological properties are specially adapted for filling and for optimal recovery of consistency. They are preferably in the form of dispersions supporting amphiphilic excipients. Said compositions enable the formulation of active liquid, pasty and even solid substances.

10 Claims, 2 Drawing Sheets

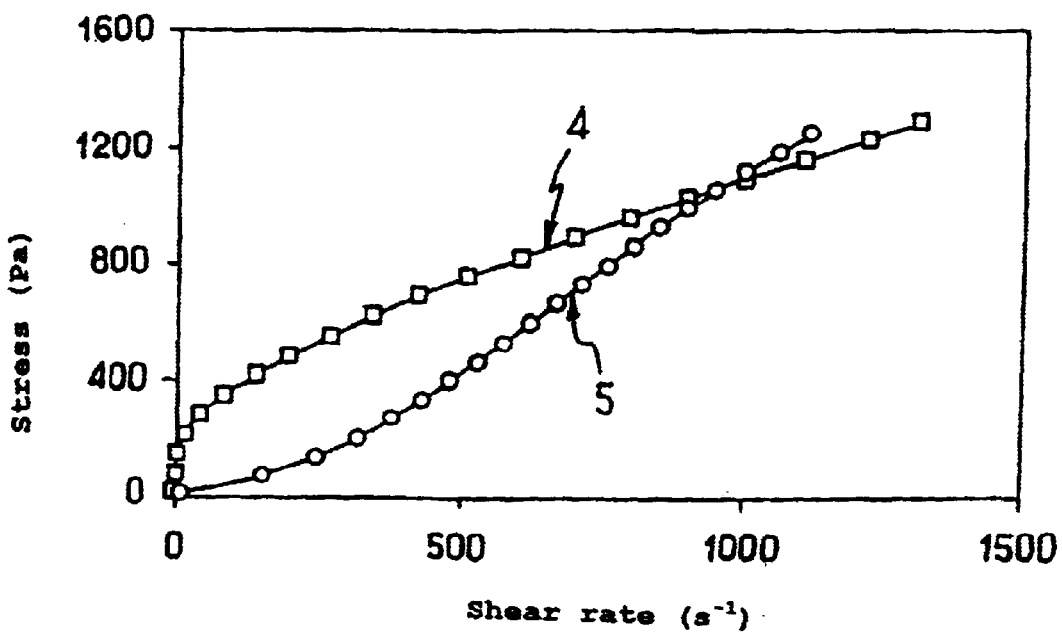
FIG_1
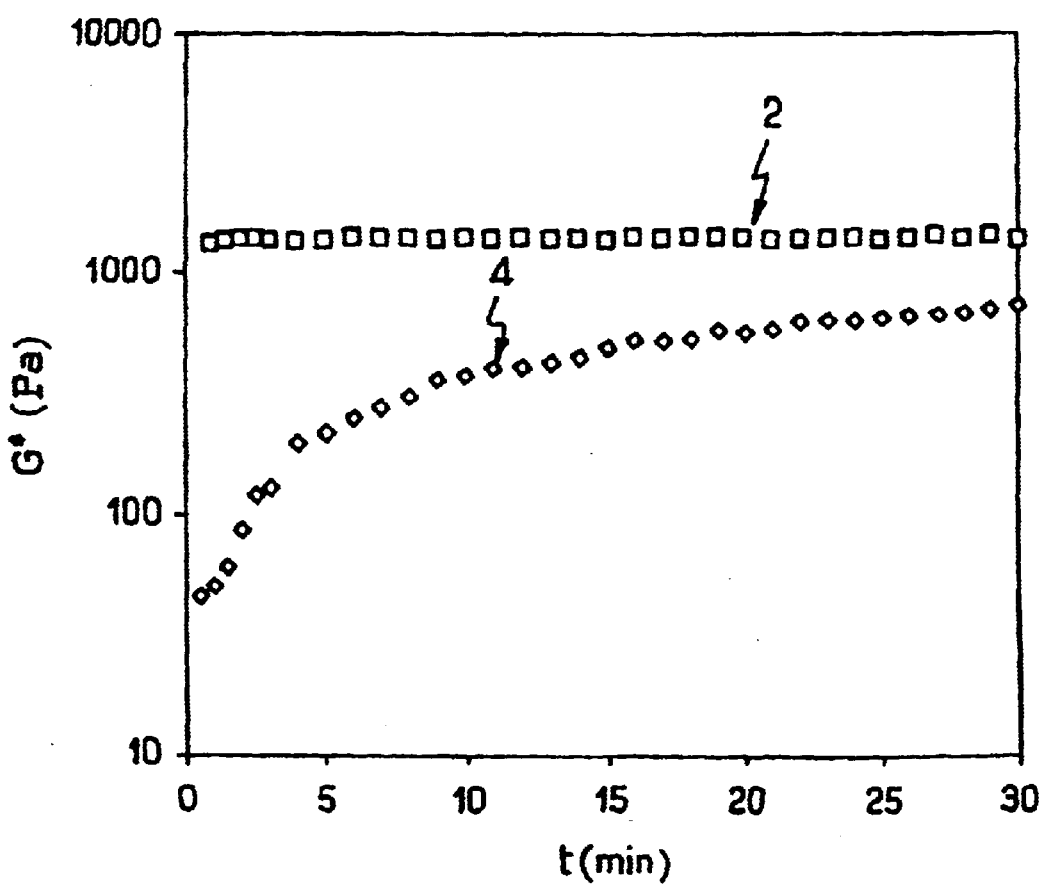
FIG_2

THIXOTROPIC FORMULATIONS FOR FILLING CAPSULES

The present invention relates to thixotropic pharmaceutical or veterinary, dietary or cosmetic compositions containing one or more active substances intended for filling capsules with a hard casing, called hard capsules, at room temperature.

The term "room temperature" is understood to mean a temperature substantially between 15 and 30° C.

Two types of capsules are used for medicinal products intended for oral, rectal or vaginal administration, namely capsules with a soft case and capsules with a hard case.

Individual liquid or pasty pharmaceutical compositions are conventionally presented in soft capsules. However, the process for manufacturing soft capsules requires the use of complex plants and specialized custom molders, so that the use of hard capsules may, for economic reasons, be preferred.

Hard capsules are conventionally used for packaging solid substances such as powders and granules. In some cases, filling hard capsules with solid substances poses certain technical problems such as, on the one hand, the generation of contaminating dust when handling active and toxic substances (anticancers, hormones)—something which may prove to be particularly dangerous—and, on the other hand, the nonuniform filling from one hard capsule to another when the active substance or substances are lightly dosed.

This is why a solid active substance may be combined with a liquid vehicle before being packaged in hard capsules (US H 672).

The use of a liquid vehicle for the filling of hard capsules also raises problems, since the liquid can flow out between the body and the top of the hard capsule. Leaks are generally avoided by sealing the hard capsules (EP 488 181 and WO-91/02520). This sealing operation requires a particular know-how and an additional step incurring a not insignificant additional cost.

An alternative to sealing the hard capsules has been proposed. It consists in filling the hard capsules with a composition containing the active principle in the dissolved or dispersed state. This same composition is liquid or pasty and of low viscosity during the filling and it then thickens inside the hard capsules.

According to a first filling mode, called "hot filling", the composition, which is pasty at room temperature, is thinned by heating (EP-49 909). This method cannot be applied to heat-sensitive active principles such as certain anticancer agents, vitamins and antibiotics.

According to a second filling mode, called "room-temperature filling", GB-1 590 864 provides compositions such that their viscosity at 20±1° C. is between 500 and 5000 mpa.s, preferably between 1000 and 3000 mPa.s, measured at 450 revolutions per minute on a Haake viscosimeter, and such that their surface tension is greater than 20 dynes/cm, preferably greater than 30 dynes/cm.

However, GB-1 590 864 does not specify what the viscosity of the compositions at rest must be.

Moreover, a third filling mode, combining the first two, has been described in EP-49 909. According to this method, a shear-thinning composition, containing liquid paraffin, hydrogenated castor oil and colloidal silica, is heated to 40° C.

The Applicant has demonstrated that the shear-thinning nature of the compositions for filling hard capsules of the prior art, although necessary for ensuring proper filling of the hard capsule, nevertheless proves to be insufficient.

This is because it is also imperative to check that the formulation at rest in the hard capsule restructures sufficiently strongly and above all sufficiently quickly, after filling, to avoid any leakage between the two parts of the hard capsule.

It is therefore absolutely essential for the consistency of the composition at rest to be sufficient to avoid any flow of the composition between the two parts of the hard capsule.

Among the raw materials that are used in conventional filling compositions are polyethylene glycols. Polyethylene glycols are intended to dissolve the water-soluble active principle of the filling composition, by virtue of their hydrophilic properties (EP-276 116, EP-488 181 and EP-49 909).

It has been found that the incorporation, as continuous phase, of polyethylene glycols, and more particularly of polyethylene glycols of low average molecular masses, in the filling composition may pose serious physicochemical interaction problems and therefore stability problems.

In particular, these polyethylene glycols are hygroscopic and attract water from the gelatin into the continuous phase making the case brittle and weak during storage.

The filling compositions of the present invention are advantageously free of any polyethylene glycol, and in particular of polyethylene glycol of low average molecular mass, which would run the risk of weakening the case of the hard capsules.

The objective of the present invention is to provide compositions termed "thixotropic" compositions containing one or more active substances which allow any filling of the hard capsules at room temperature and which ensure the absence of leaks between the two parts of the hard capsule without it being necessary to make use of the sealing usually recommended for this type of pharmaceutical dosage form.

The rheological properties of the formulations of the invention ensure effective filling at room temperature and the absence of leaks from the filled hard capsules.

It will be recalled that a liquid or pasty thixotropic composition has a shear-thinning character which is manifested by a reduction in the apparent viscosity under the effect of increasing shear. Furthermore, any variation in the shear conditions causes a structural modification delayed over time. Thus, in particular a gradual, total or partial recovery in consistency is observed after the shear has stopped.

The rheological parameters chosen as being particularly representative of the consistency of the formulations are:

the complex modulus $G^*$, the value of which is greater the thicker the product under study, which complex modulus is a synthesis of the elastic and viscous properties of the material, and the phase shift $\delta$, of between 0° and 90°, knowing that a phase shift of greater than 45° characterizes a predominantly viscous nature and, conversely, a phase shift of less than 45° demonstrates a predominantly elastic nature characteristic of a structured material.

The present invention relates to liquid or pasty thixotropic compositions containing one or more active substances, intended for filling hard capsules at room temperature, such that:

their complex modulus G* is greater than about 100 Pa, their phase shift δ is less than about 45°,
their viscosity decreases with increasing shear rate,
under the effect of a constant shear rate $\gamma_0$, the viscosity of the said compositions decreases in a delayed manner over time and stabilizes at the equilibrium value $\eta_{eq}$ of between 10 mPa.s and about 10 000 mPa.s, when $\gamma_0$ is between 100 and 1000 $s^{-1}$ and
after making the said shear rate 0, the complex modulus and the phase shift of the said compositions resume, after a time t of less than 1 hour, G* and δ values of greater than about 100 Pa and of less than about 45°, respectively.

The compositions according to the invention are therefore defined, on the one hand, by their shear-thinning nature, that is to say that their viscosity decreases when the intensity of the shear increases and, on the other hand, by the decrease in their viscosity over time for a given shear.

The formations of the invention thus thin in the hard-capsule filling machine due to the effect of the shear induced by the agitation present from the feed hopper right to the dispensing nozzle. This property makes it particular easy to fill the hard capsules.

For each shear rate, the viscosity of the compositions of the invention decreases over time and finally stabilizes at an equilibrium value denoted $\eta_{eq}$. The compositions according to the invention have equilibrium viscosities $\eta_{eq}$ at 100 $s^{-1}$ and 1000 $s^{-1}$ of between 10 mPa.s and 10 000 mPa.s, preferably between 100 mPa.s and 1500 mPa.s. It is entirely unnecessary to make use of a heating operation, as required in certain processes of the prior art (U.S. Pat. No. 4,450,877).

The compositions according to the invention are also defined by a significant recovery in consistency delayed over time.

The compositions of the invention, thinned in the hard-capsule filling machine, resume their initial consistency after a sufficient rest time, so as to avoid any risk of a leak from the full capsule.

The formulations according to the invention are characterized by G* values of greater than 100 Pa, preferably greater than 1000 Pa, and/or δ values of less than 45°, preferably less than 25°, and/or a recovery time t of less than 1 hour and preferably less than 30 minutes, and/or $\eta_{eq}$ values of between 100 mPa.s and 1500 mPa.s when the shear rate is between 100 and 1000 $s^{-1}$.

Once the recovery has been completed, $G^*_{eq}$ is greater than 100 Pa, preferably 1000 Pa, and $\delta_{eq}$ is less than 45°, preferably less than 25°.

The hard capsules used within the context of the present invention consist of gelatin, of a cellulose polymer (such as hydroxypropylmethyl cellulose) or of any other polymer capable of fulfilling the use functions of gelatin in the form of a hard capsule.

According to a preferred embodiment, the thixotropic compositions of the present invention are dispersions containing a continuous liquid or pasty dispersing phase, a viscosity-modulating dispersed phase in the particulate or micellar state and at least one active substance present in the dissolved and/or dispersed state.

The dispersing phases of the invention are characterized by their wide polarity range in terms of hydrophilic-lipophilic balance (HLB). The raw materials used in the formulation of these dispersing phases of the invention have hydrophilic, lipophilic or amphiphilic properties of variable HLB which allow the dissolution of dispersion of liquid and solid active principles which are themselves hydrophilic, lipophilic or amphiphilic.

The continuous phase of these compositions advantageously consists of at least one vehicle such as oils, their derivatives, and more particularly amphiphilic esters having an HLB of between 3 and 15, such as amphiphilic polyglycolized glycerides, like LABRASOL® and LABRAFIL® sold by Gattefosse.

The use of amphiphilic vehicles having a hydrophilic tendency represents a good alternative to the hydrophilic polyethylene glycols of the prior art. Apart from polyethylene glycols, the products conventionally used in the formulation of liquid or pasty thixotropic preparations for a hard capsule are rather lipophilic (GB-1 590 864, U.S. Pat. No. 4,450,877, US-H672, EP-461 290).

The amphiphilic continuous phases having a hydrophilic tendency used within the context of the present invention, unlike the excipients of the prior art, prove to be ideally suited to hydrophilic, lipophilic or amphiphilic active principles, whether they dissolve or disperse respectively.

The viscosity-modulating dispersed phase of the compositions according to the invention may be chosen from hydrophilic or hydrophobic pyrogenic silica particles, the mean size of which may be between 5 and 50 nm, preferably between 7 and 20 nm, and the specific surface area between 10 and 450 $m^2/g$, preferably between 70 and 410 $m^2/g$, such as AEROSIL® sold by Degussa, and ethylene oxide and propylene oxide copolymers, such as SYNPERONIC® products sold by ICI, and mixtures thereof.

The dispersed phase combined with the continuous phase makes it possible to achieve HLB values ranging up to about 20.

The viscosity-modulating dispersed phase of the compositions according to the invention preferably represents from 1 to 30% m/m, more preferably from 5 to 15% m/m, of the preparation.

The excipients used in the formulation of the thixotropic compositions according to the invention are chosen from pharmaceutically acceptable excipients that are inert with respect to the active substances that it is desired to formulate.

Furthermore, these excipients are chosen from excipients that are compatible with the casing of the hard capsules.

The excipients which are used in the formulation of the thixotropic compositions according to the invention are advantageously endowed with hydrophilic, lipophilic or amphiphilic properties with, for these, a variable hydrophilic-lipophilic balance (HLB), which allow the dissolution or dispersion of both hydrophilic and lipophilic active substances. The HLB of the vehicles may vary from 4±1 for a combination of LABRAFIL® M1944CS and AEROSIL® to 20±1 for a combination of LABRASOL® and SYNPERONIC®.

The compositions according to the invention contain an active substance which may be liquid or pasty but also solid, for example milnacipran hydrochloride (solubility in water of 600 g/l), baquimast (solubility in water of 0.23 g/l), nifedipine, triamterene, aluminum hydroxychloride, sodium salicylate, vancomycin, paramethadone and griseofulvin.

The hard capsules used within the context of the present invention consist of gelatin or of any cellulose polymer capable of fulfilling the functions of the use of gelatin in the form of a hard capsule, such as hydropropylmethyl cellulose.

The invention is not limited to these examples and a person skilled in the art will be easily able to include any active substance of his choice, whether liquid, pasty or even solid, in the compositions described.

The present invention also relates to the use of the compositions described above in a cosmetic, dietary, pharmaceutical or veterinary preparation.

BRIEF DESCRIPTION OF DRAWINGS

The present invention is illustrated by the following examples with reference to the appended figures:

FIG. 1 shows the rheogram of a formulation of example 4 of the invention and the rheogram of a composition of example 5, the rheological properties of which do not meet the criteria of the invention. The stress (in pascals) is plotted on the y-axis and the shear rate (in $s^{-1}$) is plotted on the x-axis;

FIG. 2 gives the time dependence of the recovery in consistency of two formulations of the invention, that of example 2 and that of example 4.

Figure 3:
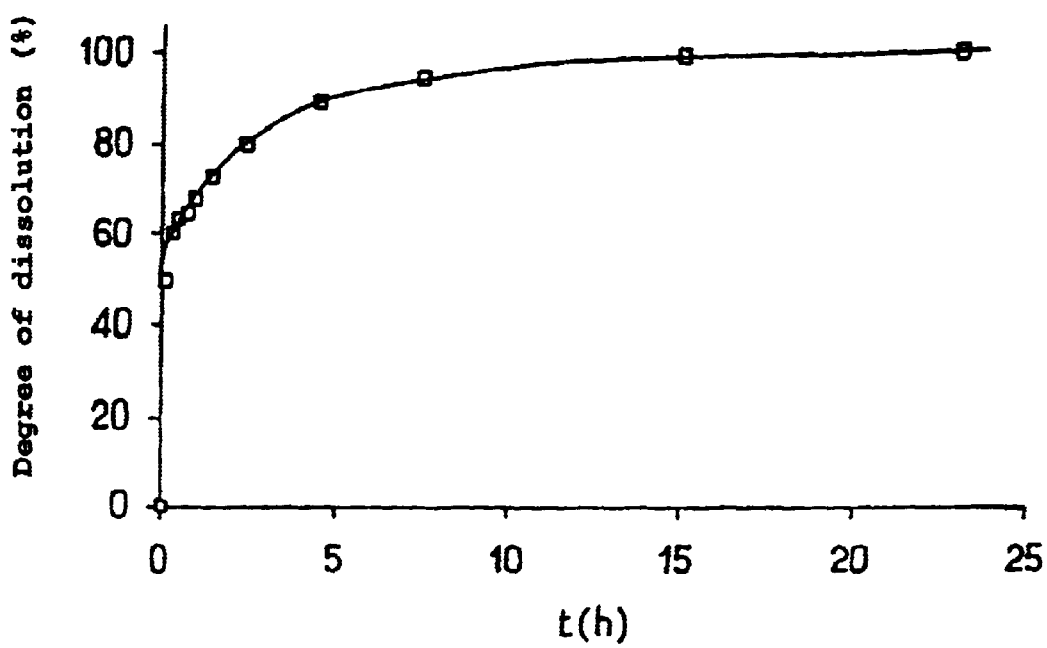
Figure 4:
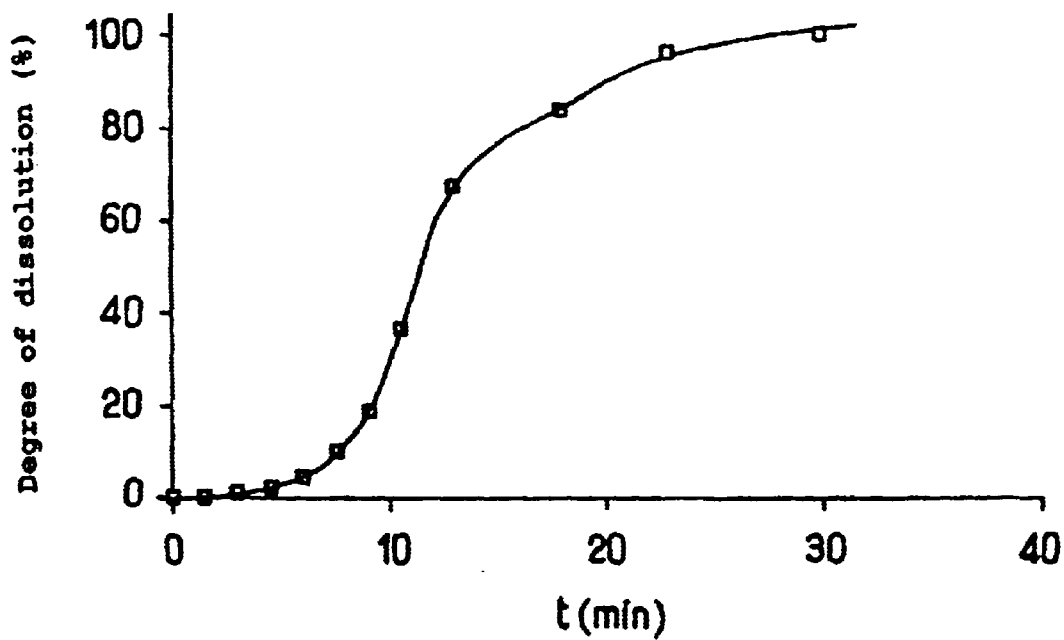

The complex modulus, expressed in pascals, is plotted on the y-axis and the time is plotted on the x-axis;

FIGS. 3 and 4 represent the degree of dissolution as a percentage (on the y-axis) of a formulation of example 1 and of a formulation of example 2, respectively, as a function of time (on the x-axis) expressed in hours and in minutes, representively.

EXAMPLES 1 TO 7 a) Preparation of the Dispersions

Seven dispersions were prepared, each containing a continuous phase, a dispersed phase and an active phase.

The continuous phase consisted of an amphiphilic ester such as LABRAFIL M1944CS® (HLB=4±1) or LABRASOL® (HLB=14±1). It should be mentioned at this stage that the amphiphilic esters that can be used within the context of the invention may have HLB values of between 3 and 15.

The dispersed phase was chosen from AEROSIL 200 V® (a hydrophilic pyrogenic silica), AEROSIL R 974® (a hydrophobic pyrogenic silica) and SYNPERONIC PE/F 68® (an ethylene oxide/propylene oxide copolymer having an HLB of 29±1). When the dispersed phase chosen was SYNPERONIC®, the HLB of the dispersing phase increased to about 20.

The active substance was chosen from milnacipran hydrochloride (a solid whose solubility in water is 600 g/l) and baquimast (a solid whose solubility in water is 0.23 g/l).

The preparations containing pyrogenic silica as dispersed phase were obtained by gradually adding silica to the amphiphilic ester with vigorous stirring, advantageously at between 1000 and 3000 revolutions per minute. The mixture was then put under vacuum and the stirring continued after incorporating the silica until homogeneous. The preparations containing SYNPERONIC® as dispersed phase were obtained by gradually adding SYNPERONIC® to the amphiphilic ester with moderate stirring, advantageously at between 400 and 800 revolutions per minute. The mixture was then put under vacuum and the stirring continued until homogeneous.

Whether the preparations contained AEROSILO® or SYNPERONIC® as viscosity-modulating dispersed phase, the active substance chosen was always added to the amphiphilic ester/dispersed phase mixture at room temperature with moderate stirring. The composition of each dispersion is given in detail in table I below.

b) Rheological Properties

The rheological properties of the seven preparations were then studied in terms of shear thinning and of recovery in consistency. b1) The shear thinning is characterized at 25° C. in terms of flow rheology in a rotating controlled-stress rheometer (Carri-Med CSL100).

The "stress as a function of shear rate" rheogram is plotted for each of the dispersions. The rheogram makes it possible to check the ability of a preparation to undergo thinning when the intensity of the shear increases.

Since the viscosity is defined as the ratio of the stress to the shear rate, a convex curve is an expression of a decrease in the viscosity with shear rate, that is to say a shear-thinning behavior, whereas a concave curve is an expression of an increase in the viscosity with shear rate, i.e. a shear-thickening behavior.

FIG. 1 shows the rheogram for two dispersions, dispersion 4 and dispersion 5, the compositions of which are given in table I above. The line of the rheogram for dispersion 4, which is convex, means that dispersion 4 is shear thinning and meets one of the criteria of the compositions of the invention, whereas that for preparation 5, which is concave, demonstrates its shear-thickening character.

Table I specifies the observed shear-thinning or shear-thickening character in light of the rheogram for each dispersion.

The formulations were also subjected to constant shear rates of the same order of magnitude as those involved in a hard-capsule filling machine of conventional type (100 $s^{-1}$ for the lines in the machine and 1000 $s^{-1}$ for the narrowing at the exit of the injection nozzle).

For each shear rate, it may be seen that there is a reduction in the viscosity over time, which finally stabilizes at an equilibrium value denoted $\eta_{eq}$. The results are given in table I.

The seven dispersions have equilibrium viscosities, at a shear rate of 100 $s^{-1}$ or 1000 $s^{-1}$, of between 100 mPa.s and 5000 mPa.s.

These viscosity values consequently prove to be suitable for the automatic filling of hard capsules. It is entirely unnecessary to thin our thixotropic dispersions further by raising the filling temperature, as recommended by the authors of patent U.S. Pat. No. 4,450,877. b2) The rheological conditions relating to the resumption of thixotropy, and which guarantee that there are no leaks long term, were determined at 25° C., in dynamic rheology, in a controlled-stress Couette-type rotating rheometer (Carri-Med CSL 100).

This mode of study, unlike flow rheology, allows the consistency of a material "at rest" to be assessed since it is possible to apply appreciably smaller strains to the material than in flow.

The seven dispersions were presheared for 15 minutes at 1000 s$^{-1}$.

The parameters used to characterize the recovery in consistency are the magnitude of the recovery (expressed as a percentage), the complex modulus G* (in pascals) after recovery and the phase shift δ (in degrees) 1 hour after stopping the shear and the time $t_{50\%}$ for the recovery to reach 50% with respect to $G^*_{eq}$. The results are summarized in table I above.

The percentage recovery in consistency of the shear-thinning dispersions 1, 2, 3, 4, 6 and 7 is equal to 100%. The recovery is therefore total. The values of the G* recovery after 1 hour are total and greater than 100 Pa in respect of preparations 1, 4 and 7, but less than 100 Pa in respect of preparations 5 and 6, which reach values of 5 and 70 Pa, respectively.

After recovery, δ is less than 25° for all the dispersions, with the exception of dispersion 5 (equal to 71°)

For the five shear-thinning dispersions, $t_{50\%}$ is less than 30 minutes.

Dispersions 1, 2, 3, 6 and 7 therefore undergo rapid and total recovery in their consistency, which furthermore is considerable.

FIG. 2 shows the change in G* as a function of time for dispersions 2 and 4. It may be seen that the recovery in consistency of dispersion 2 is very rapid ($t_{50\%}$ 1 s) and considerable (after recovery G*=1400 Pa), that of dispersion 4 is slower ($t_{50\%}$=23 min.) and considerable (after recovery G*=900 Pa).

c) Hard-capsule Stability Study

Having studied the rheological properties of the dispersions, they were dispensed into size-1 conventional-closure hard gelatin capsules at room temperature using an industrial-type filling machine. The filling was carried out with a coefficient of variation in the mass of the filled hard capsule which was systematically less than 1.5%.

The filled hard capsules were stored for 12 months in an oven (25° C.±2° C. and 60% RH±5% RH) in order to confirm that there were no leaks and no deformation in the casing of the capsule. Only the capsules containing preparations 5 and 6 had leaks during storage.

d) Hard-capsule In Vitro Release Study

In vitro release studies, performed in a "Dissolutest" (water at 37±0.5° C., 100 tpm), were carried out. The results for preparations 1 and 2 are given in FIGS. 3 and 4, respectively.

The release of milnacipran hydrochloride (a solid water-soluble active principle) is more rapid the more hydrophilic the continuous phase.

Under the operating conditions employed, preparation 2 (FIG. 4) containing an amphiphilic ester having a hydrophilic tendency (HLB=14) releases the active principle very much more rapidly than preparation 1 (FIG. 3) containing an amphiphilic ester having a lipophilic tendency (HLB=4±1).

The choice of continuous phase therefore makes it possible to tailor the rate of release of the active principle.

TABLE I

COMPOSITIONS AND CRITICAL RHEOLOGICAL PARAMETERS OF THE DISPERSION EXAMPLES

| | Formulation: | | | Thixotropy characterization | | | | | | |
|---|---|---|---|---|---|---|---|---|---|---|
| | Continuous phase | | | Shear thinning | | | Recovery in thixotropy | | | Stability: |
| Examples | Dispersed phase Active principle (% m/m) | | | Rheogram Stress = f (rate) | $\eta_{eq}$ at 100 s$^{-1}$ (mPa · s) | $\eta_{eq}$ at 1000 s$^{-1}$ (mPa · s) | Extent of the recovery (%) | G* after recovery (Pa) | δ after recovery (*) | 150% | 25 ± 2° C.: 60% ± 5% RH (12 months) |
| 1 | LABRAFIL M1944CS ® AEROSIL 200V ® Milnacipran hydrochloride | 90% 10% 4% | 96% | Shear-thinning | 710 | 360 | 100 | 3100 | 5 | 21 s | Stable |
| 2 | LABRASOL ® AEROSIL 200V ® Milnacipran hydrochloride | 94 6% 4% | 96% | Shear-thinning | 390 | 190 | 100 | 1400 | 8 | 1 s | Stable |
| 3 | LABRASOL ® SYNPERONIC PE/F68 ® Milnacipran hydrochloride | 88% 12% 7% | 93% | Shear-thinning | 810 | 600 | 100 | 2100 | 17 | 12 min | Stable |
| 4 | LABRAFIL M1944CS ® AEROSOL R974 ® BAQUIMAST ® | 90% 10% 5% | 95% | Shear-thinning | 1020 | 980 | 100 | 900 | 12 | 23 min | Stable |
| 5 | LABRASOL ® AEROSIL R974 ® Milnacipran hydrochloride | 90% 10% 4% | 96% | Shear-thickening | 510 | 1100 | — | 5 | 71 | — | Leaks |
| 6 | LABRAFIL M1944CS ® AEROSIL 200V ® Milnacipran hydrochloride | 96% 4% 4% | 96% | Shear-thinning | 140 | 110 | 100 | 70 | 21 | 6 s | Leaks |

TABLE I-continued

COMPOSITIONS AND CRITICAL RHEOLOGICAL PARAMETERS OF THE DISPERSION EXAMPLES

| | Formulation: | | | | Thixotropy characterization | | | | | |
|---|---|---|---|---|---|---|---|---|---|---|
| | Continuous phase | | | Shear thinning | | | Recovery in thixotropy | | | Stability: |
| Examples | Dispersed phase Active principle (% m/m) | | | Rheogram Stress = f (rate) | $\eta_{eq}$ at 100 s$^{-1}$ (mPa·s) | $\eta_{eq}$ at 1000 s$^{-1}$ (mPa·s) | Extent of the recovery (%) | G* after recovery (Pa) | δ after recovery (*) | 150% | 25 ± 2° C.: 60% ± 5% RH (12 months) |
| 7 | LABRASOL ® SYNPERONIC PE/F68 ® Milnacipran hydrochloride | 70% 30% 4% | 96% | Shear-thinning | 4800 | 2300 | 100 | 18,780 | 12 | 12 min | Stable |

What is claimed is:

1. Liquid or pasty thixotropic compositions which contain a continuous dispersing phase, a dispersed phase and one or more active substances, intended for filling hard capsules at room temperature, wherein:

their complex modulus G* is greater than about 100 Pa, their phase shift δ is less than about 45°, their viscosity decreases with increasing shear rate, under the effect of a constant shear rate $\gamma_o$, the viscosity of the said compositions decreases in a delayed manner over time and stabilizes at the equilibrium value $\eta_{eq}$ of between 10 mPa.s and about 10,000 mPa.s, when $\gamma_o$ is between 100 and 1000 s$^{-1}$ and after making the said shear rate 0, the complex modulus and the phase shift of the said compositions resume, after a time t of less than 1 hour, G* and δ values of greater than about 100 Pa and of less than about 45°, respectively, and wherein the continuous phase consists of at least one vehicle selected from amphiphilic esters having an HLB between 3 and 15.

2. A composition according to claim 1, wherein:

G* is greater than 1000 Pa, and/or

δ is less than 25° and/or $\eta_{eq}$ is between 100 and 1500 mPa.s when $\gamma_o$ is between 100 and 1000 s$^{-1}$ and/or t is less than 30 min.

3. A composition according to claim 1, wherein the dispersed phase is selected from the group consisting of hydrophilic or hydrophobic pyrogenic silica particles and ethylene oxide/propylene oxide copolymers, the latter making it possible to achieve, when combined with the continuous phase, HLB values ranging up to about 20.

4. A composition according to claim 1, wherein the active substance is liquid, pasty or solid.

5. A composition according to claim 4, wherein the active substance is selected from the group consisting of milnacipran hydrochloride, baquimast, nifedipine, triamterene, aluminum hydroxychloride, sodium salicylate, vancomycin, paramethadone and griseofulvin.

6. A composition according to claim 1, wherein the dispersed phase of the preparations according to the invention represent 1 to 30% m/m of the preparation.

7. A composition according to claim 6, wherein the dispersed phase of the dispersions according to the invention represent from 5 to 15% m/m of the preparation.

8. A composition according to claim 1, wherein the amphiphilic ester is a polyglycolized glyceride.

9. A hard capsule consisting of gelatin or of any cellulose polymer capable of fulfilling the functions of gelatin, said hard capsule having the composition of claim 1 as a filling.

10. A hard capsule consisting of hydroxypropylmethylcellulose, said hard capsule having the composition of claim 1 as a filling.

* * * * *

UNITED STATES PATENT AND TRADEMARK OFFICE
CERTIFICATE OF CORRECTION

PATENT NO.   : 6,709,675 B1
DATED        : March 23, 2004
INVENTOR(S)  : Pascal Lombardin et al.

It is certified that error appears in the above-identified patent and that said Letters Patent is hereby corrected as shown below:

Column 10,
Line 24, "claim 4" should be -- claim 1 --.
Line 32, "claim 6" should be -- claim 1 --.

Signed and Sealed this

Fifteenth Day of February, 2005

JON W. DUDAS
*Director of the United States Patent and Trademark Office*